(12) United States Patent
Yang

(10) Patent No.: US 9,226,656 B2
(45) Date of Patent: Jan. 5, 2016

(54) REAL-TIME OPTICAL AND DIGITAL IMAGE STABILIZATION FOR ADAPTIVE OPTICS SCANNING OPHTHALMOSCOPY

(71) Applicant: Qiang Yang, Rochester, NY (US)

(72) Inventor: Qiang Yang, Rochester, NY (US)

(73) Assignees: University of Rochester, Rochester, NY (US); Montana State University, Bozeman, MT (US)

( * ) Notice: Subject to any disclaimer, the term of this patent is extended or adjusted under 35 U.S.C. 154(b) by 0 days.

(21) Appl. No.: 14/483,289

(22) Filed: Sep. 11, 2014

(65) Prior Publication Data

US 2015/0077706 A1  Mar. 19, 2015

Related U.S. Application Data

(60) Provisional application No. 61/879,961, filed on Sep. 19, 2013.

(51) Int. Cl.
*A61B 3/10* (2006.01)
*A61B 3/14* (2006.01)
*A61B 3/00* (2006.01)
*A61B 3/12* (2006.01)

(52) U.S. Cl.
CPC .............. *A61B 3/1025* (2013.01); *A61B 3/0025* (2013.01); *A61B 3/12* (2013.01)

(58) Field of Classification Search
USPC .................................................. 351/200–246
See application file for complete search history.

(56) References Cited

U.S. PATENT DOCUMENTS

| | | | |
|---|---|---|---|
| 2013/0194548 A1* | 8/2013 | Francis | A61B 3/1025 351/208 |
| 2013/0215385 A1* | 8/2013 | Hirose | A61B 3/1025 351/206 |

* cited by examiner

*Primary Examiner* — Mohammed Hasan
(74) *Attorney, Agent, or Firm* — Harris Beach PLLC

(57) ABSTRACT

A real-time ophthalmoscope system for imaging an eye includes a wide field scanning light ophthalmoscope (SLO) configured for wide field imaging of the eye. The system also includes a small field SLO configured for high resolution imaging of the eye. A 2D tracking minor electrically coupled to a computer, and a 2D steering minor electrically coupled to the computer, are both disposed in an optical path between the small field SLO and the eye. The system is configured to acquire a plurality of small field images at a plurality of locations on the eye as defined by the 2D steering minor, each of the small field images is stabilized for a motion of the eye by the 2D tracking minor. A method for imaging of the eye is also described.

15 Claims, 7 Drawing Sheets

REAL-TIME OPTICAL AND DIGITAL IMAGE STABILIZATION FOR ADAPTIVE OPTICS SCANNING OPHTHALMOSCOPY

CROSS-REFERENCE TO RELATED APPLICATIONS

This application claims priority to and the benefit of U.S. provisional patent application Ser. No. 61/879,961, REAL-TIME OPTICAL AND DIGITAL IMAGE STABILIZATION FOR ADAPTIVE OPTICS SCANNING OPHTHALMOSCOPY, filed Sep. 19, 2013, which application is incorporated herein by reference in its entirety.

STATEMENT REGARDING FEDERALLY SPONSORED RESEARCH OR DEVELOPMENT

This invention was made with government support under contract EY014375 (Biomedical Research Partnership) awarded by National Institutes of Health (NIH). The government has certain rights in the invention.

TECHNICAL FIELD

The application relates to scanning ophthalmoscopy and particularly to image stabilization in scanning ophthalmoscopy.

BACKGROUND

In the field of ophthalmoscopy, eye motion remains a major impediment to the efficient acquisition of high quality retinal images.

SUMMARY

According to one aspect, a real-time ophthalmoscope system for imaging an eye includes a wide field scanning light ophthalmoscope (SLO) electrically coupled to a computer. The wide field SLO is configured for wide field imaging of the eye. A small field SLO is also electrically coupled to the computer. The small field SLO is configured for high resolution imaging of the eye. A 2D tracking mirror is electrically coupled to the computer and is disposed in an optical path between the small field SLO and the eye. A 2D steering mirror is electrically coupled to the computer and is also disposed in the optical path between the small field SLO and the eye. The system is configured to acquire a plurality of small field images at a plurality of locations on the eye as defined by the 2D steering mirror, each of the small field images is stabilized for a motion of the eye by the 2D tracking minor.

In one embodiment, the system further includes a closed loop control of the tracking minor by the small field SLO.

In another embodiment, the 2D tracking minor is further disposed in an optical path between the wide field SLO and the eye, and further including a closed loop control of the tracking minor by the wide field SLO.

In yet another embodiment, the 2D tracking mirror includes a Tip/tilt minor.

In yet another embodiment, a position of the tracking minor is updated at a rate of about 1 kHz.

In yet another embodiment, at least one of the small field SLO computer and the wide field SLO computer further includes a graphics processing unit (GPU).

In yet another embodiment, the wide field SLO is synchronized with the small field SLO.

In yet another embodiment, the small field SLO includes an adaptive optics scanning light ophthalmoscope (AOSLO).

In yet another embodiment, the wide field SLO includes wide field scanning light ophthalmoscope (WFSLO).

In yet another embodiment, the computer includes a wide field SLO computer and a small field SLO computer, and the wide field SLO is electrically coupled to a wide field SLO computer. The small field SLO is electrically coupled to the small field SLO computer which is communicatively coupled to the wide field SLO computer. The 2D tracking minor is electrically coupled to the wide field SLO computer and the 2D steering minor is electrically coupled to the small field SLO computer.

In yet another embodiment, the wide field SLO is synchronized with the small field SLO.

According to another aspect, a method for imaging an eye including the steps of: a) providing a wide field scanning light ophthalmoscope (SLO) electrically coupled to a computer, the wide field SLO configured for wide field imaging of the eye, a small field SLO electrically coupled to the computer communicatively coupled to the wide field SLO computer, the small field SLO configured for high resolution imaging of the eye, a 2D tracking minor electrically coupled to the computer and disposed in an optical path between the small field SLO and the eye, and a 2D steering mirror electrically coupled to the computer and also disposed in the optical path between the small field SLO and the eye; b) pointing the small field SLO at a location on the eye to be imaged; c) stabilizing the small field SLO against a movement of the eye by use of the 2D tracking mirror controlled by at least the wide field SLO; d) imaging the location by the small field SLO to provide a stabilized image of the location; e) repeating steps b to d until a desired number of the stabilized images of a plurality of locations are obtained; and f) montaging a plurality of the images to form a stabilized image of the eye.

In one embodiment, the method further includes after step d, the step of stabilizing further the stabilized image by a digital stabilization method.

In another embodiment, the digital stabilization method is performed in software.

In another embodiment, the step c further includes stabilizing the small field SLO against a movement of the eye by use of the 2D tracking mirror controlled by both the small field SLO and the wide field SLO.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

DETAILED DESCRIPTION

Figure 1:
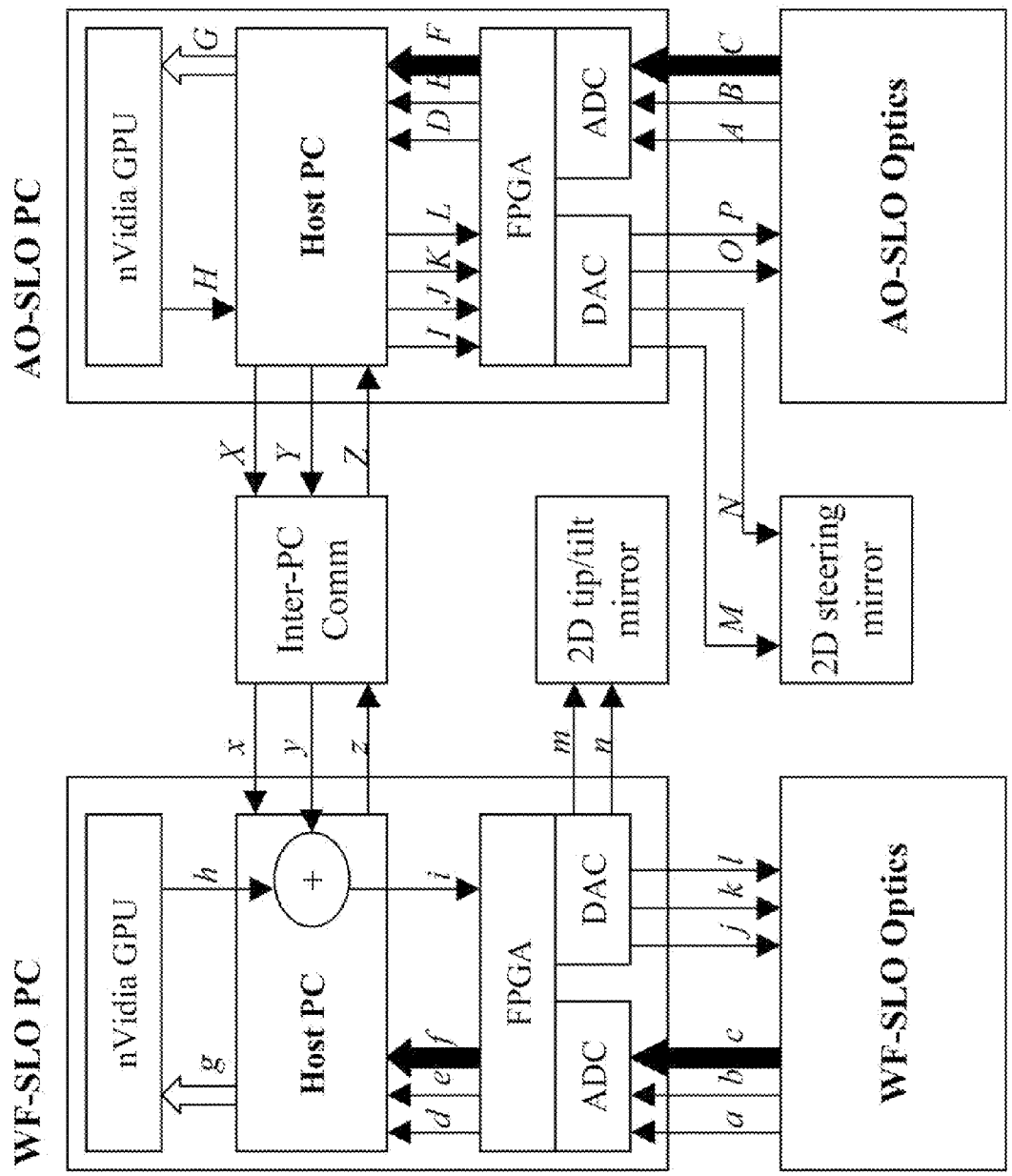
FIG. 1 shows a block diagram of an exemplary embodiment of a hybrid real-time eye tracking system.

Eye motion is a major impediment to the efficient acquisition of artifact-free high resolution retinal images with the adaptive optics scanning light ophthalmoscope (AOSLO). We describe hereinbelow a solution to this problem that combines both optical and digital image stabilization in an AOSLO by use of both a small field ASLO and a wide field SLO (WFSLO). The usual pupil conjugate slow scanner in the AOSLO is replaced by a 2D fast tip/tilt mirror that has the dual functions of slow scanning and optical eye tracking. The closed-loop optical tracking demonstrated is capable of reducing the amplitude of fixational eye motion by a factor of about 2 to 4 dependent on the mechanical response of the 2D tip/tilt mirror. The optical tracking is capable of correcting the frequency of eye motion up to N/2 Hz where N is the frame rate of the imaging system. The real-time digital stabilization picks up the residual eye motion with a subpixel accuracy of 0.4 µm to about 0.8 µm. The current implementation still suffers the disadvantage of 'frame-out' where the control algorithm has difficulty resetting the position of the tracking mirror after a saccade or blink. We are integrating a wide field-of-view (FOV) system, with about a 20° to 30° scanning angle, to solve this problem. It is contemplated that, the wide-FOV system will join eye tracking so that the integrated system is capable of significantly improving efficiency of AOSLO imaging in both normal and diseased eyes even with poor fixation due to retinal diseases.

There are two existing technologies for eye tracking: a wide field-of-view (FOV) system such as SLO (10-30 degrees), or a small FOV system such as AOSLO (1-2 degree). SLO is capable of covering large eye motion but lacks spatial resolution. AOSLO has a high spatial resolution capability, however, can suffer "frame out" where the target frame moves out of the reference frame and causes image registration to fail. Therefore, it is difficult to implement either one of them in real time.

The current solutions usually sample large volumes of videos, and then post process them tediously, or call offline image registration. In the system and method described herein, a new apparatus is contemplated which combines WFSLO and AOSLO into a hybrid tracking system where a tracking mirror is added into the optical system, to remove large eye motion on the AOSLO. A large eye motion signal is obtained from the wide FOV system which has low resolution. After the correction from the tracking mirror, the residual eye motion on the small FOV system can be reduced to about 20 µm to 50 µm, which can be registered efficiently with a fast GPU registration algorithm. Currently there is no effective solution to do real-time high-resolution eye tracking and registration.

One previous work on real-time eye tracking with a large FOV line scanning system was based on hardware alone. The application of such previous hardware only solutions were found to be limited. Hardware tracking was found to succeed only occasionally and not reliably over time. Also, there was no communication between the wide FOV system and the small FOV system, and the small FOV system did not do additional real-time tracking to remove the residual eye motion.

There are several advantages of the new apparatus described herein over apparatus and methods of the prior art. For example, it is contemplated that the small FOV system and the wide FOV system can be integrated, and that the scanners on the two systems can be synchronized with the same driving signals. Also, high resolution images from the small FOV system with residual eye motion can be registered and montaged in real time. It is also believed that by use of the new apparatus described herein that RMS error can be reduced to less than 2 micrometers. For clinical applications, it is believed that the new apparatus described herein can dramatically reduce patients' clinical imaging time from several hours to 20 to 30 minutes, as well as allow new research aiming at new eye diseases. It is also believed that this solution can make possible high-resolution eye laser surgery with an accuracy of about several micrometers. For scientific applications, it is believed that new apparatus described herein can allow scientists to track retinal positions efficiently and accurately inside the wide FOV. Moreover, this solution will eliminate tedious post processing of huge volumes of videos.

FIG. 1 is a block diagram showing a flow chart of control signals for one exemplary embodiment of the new real-time ophthalmoscope system. As contemplated, wide field scanning light ophthalmoscope (WFSLO) is shown electrically coupled to a wide field SLO computer. A small field scanning light ophthalmoscope (AOSLO) is shown electrically coupled to a small field SLO computer. The small field SLO is configured to acquire a plurality of high resolution small field images at a plurality of locations on an eye as defined by a 2D steering mirror. During each acquisition of a small field image, a 2D tracking mirror (shown in FIG. 1 as a 2D tip/tilt mirror) provides image stabilization to compensate for eye movement. Both of the 2D tracking mirror and the 2D steering mirror are disposed in the optical path (order independent) between the small field SLO and the eye.

Continuing with FIG. 1, control signal notations are as follows: a: horizontal synchronization signal from WFSLO resonant scanner; b: vertical synchronization signal from WFSLO slow scanner; c: one or more analog video signals from WFSLO photodetector(s); d: Digitized WFSLO horizontal synchronization signal to the host PC; e: Digitized WFSLO vertical synchronization signal to the host PC; f: WFSLO digitized video signals to the host PC; g: WFSLO digitized video signal to the GPU for calculating eye motion; h: Calculated eye motion signal based on WFSLO images; i: Synthesized eye motion signal from both WFSLO and AOSLO; j: Signal to control WFSLO resonant scanner; k: Signal to control WFSLO slow scanner; l: Signals to control other WFSLO parameters; m: Analog eye motion signal to control the 2D tip/tilt mirror, in horizontal direction; n: Analog eye motion signal to control the 2D tip/tilt mirror, in vertical direction; x: Digital signals passed from AOSLO, e.g., end of frame, AOSLO success/fail flag, etc.; y: Digital eye motion signals passed from AOSLO; z: Digital signals passed to AOSLO, e.g., WFSLO success/fail flag; A: horizontal synchronization signal from AOSLO resonant scanner; B: vertical synchronization signal from AOSLO slow scanner; C: multiple channels of analog video signals from AOSLO photodetectors; D: Digitized AOSLO horizontal synchronization signal to the host PC; E: Digitized AOSLO vertical synchronization signal to the host PC; F: AOSLO digitized video signals to the host PC; G: AOSLO digitized video signal to the GPU for calculating eye motion; H: Calculated eye motion signal based on AOSLO images; I: digital signal for the steering mirror, horizontal control; J: digital signal for the steering mirror, vertical control; K: digital signals for controlling AOSLO resonant scanner and slow scanner; L: digital signals for AOSLO stimulation and other external devices; M: analog signal for the steering mirror, horizontal control; N: analog signal for the steering mirror, vertical control; O: analog signals for controlling AOSLO resonant scanner and slow scanner; P: analog signals for AOSLO stimulation and other external devices; X: Digital signals passed to WFSLO, e.g., end of frame, AOSLO success/fail flag, etc.; Y: Digital eye motion signals passed to WFSLO; Z: Digital signals passed from WFSLO, e.g., WFSLO success/fail flag; circle with plus sign: Signal synthesizer, with ⊕: Signal synthesizer, with $i = g_1*h + g_2*y$, where $g_1$ is the control gain of WFSLO and $g_2$ is the control gain of AOSLO, for the 2D tip-tilt mirror.

Motion detection and tracking of motion of the eye for imaging an eye as performed herein is generally based on comparing a movement of any suitable feature of the eye having a suitable contrast for tracking over time. Typically motion tracking (for control of the 2D tip/tilt minor) is updated every 1 millisecond during imaging by the small field SLO. While the contemplated WFSLO system is dedicated to motion tracking, as explained in more detail below, the system typically also considers information from the AOSLO system data (i.e. both wide field (e.g. WFSLO) and small field (e.g. AOSLO) data are typically used for motion tracking. For example small field AOSLO line scan data, such as for example, a strip of several line scans (e.g. about 8 to 16 lines, a small subset of a frame) can be used to develop motion tracking information to more finely set the position of the 2D tip/tilt minor to track residual eye motion. Thus, as described hereinabove, a large eye motion signal can be obtained from the wide FOV system which has low resolution. After the correction from the tracking mirror, the residual eye motion on the small FOV system can be reduced to 20 μm to 50 μm, which can be registered efficiently with a fast GPU registration algorithm. Such motion tracking processes can be performed substantially in read-time.

example: Turning to FIG. 1, information from the WFSLO (wide field) system is used by the WFSLO PC at inputs d, e, and f at the host PC, and following computation by a wide field motion image processing algorithm and processing by the graphics processing unit (GPU), the calculated wide field motion information is summed with input y from the Inter-PC communication which represent a calculated small field motion information from the small field AOSLO host PC. As described hereinabove, $i = g_1*h + g_2*y$, where $g_1$ is the control gain of WFSLO and $g_2$ is the control gain of AOSLO, and i is the control signal for the 2D tip-tilt mirror position. Continuing with the example, i is converted to two control signals by the WFSLO FPGA and converted to suitable analog control signals m and n to position the 2D tip/tilt mirror responsive (e.g. every 1 ms) to track eye motion.

The AOSLO small field system is a high resolution imaging system. When aimed or pointed at a given location (e.g. a location on the eye), it can generate an image pixel by pixel over successive scanned lines for that location. While a particular size of the image is unimportant to the system and method, about a 13-15 degree scan line deflection has been found to be useful for small field imaging of the eye.

The purpose of the 2D steering mirror is to allow the AOSLO system to image any small field area at a specific location on the eye as "steered" to that location by the positioning of the 2D steering mirror. Note that the function of the 2D steering mirror is typically to select the location to be imaged, while any associated successive line scanning to form the image (e.g. by scanning the LASER light pixel by pixel across successive lines) is performed by the AOSLO system optics itself as controlled by the AOSLO electronics. Also, note that the AOSLO LASER light also travels to and from the eye as reflected light via the 2D Tip/tilt mirror. It is the operation of the 2D Tip/tilt mirror which initially corrects the small field imaging for eye motion by hardware.

For eye scanning safety reasons, LASERs such as the LASER of a small field AOSLO have relatively low power, typically in the 100 μW to 150 μW optical power range. Therefore each image at each location, as determined by the 2D steering mirror, is generally created from many individually scanned frames. Typically 100 to 500 frames are imaged per location to increase the signal to noise ratio (S/N) of a combined image. Thus a plurality of frames for each location can be digitally processed to not only increase S/N, but also to effectively increase the image resolution. Such digital post-processing for each small field image can also be used to further reduce motion artifact, ultimately providing a small field image resolution less than 1 μm.

Typically, once a high resolution imaging location is set by positioning the 2D steering minor, the motion tracking loop becomes active, updating the position of the 2D Tip/tilt mirror at a relatively fast rate (e.g. 1 kHz) to track motion of the eye for the purpose of stabilizing the image despite any motion of the eye. Typically the subject being scanned is given a fixed target to stare at, and eye motion generally stays within a 2 to 3 degree range during imaging. Present versions of the apparatus under test can track motion to about 4 degrees, however it is contemplated that a wider range of eye motion can be accommodated using the same architecture described herein.

Figure 2:
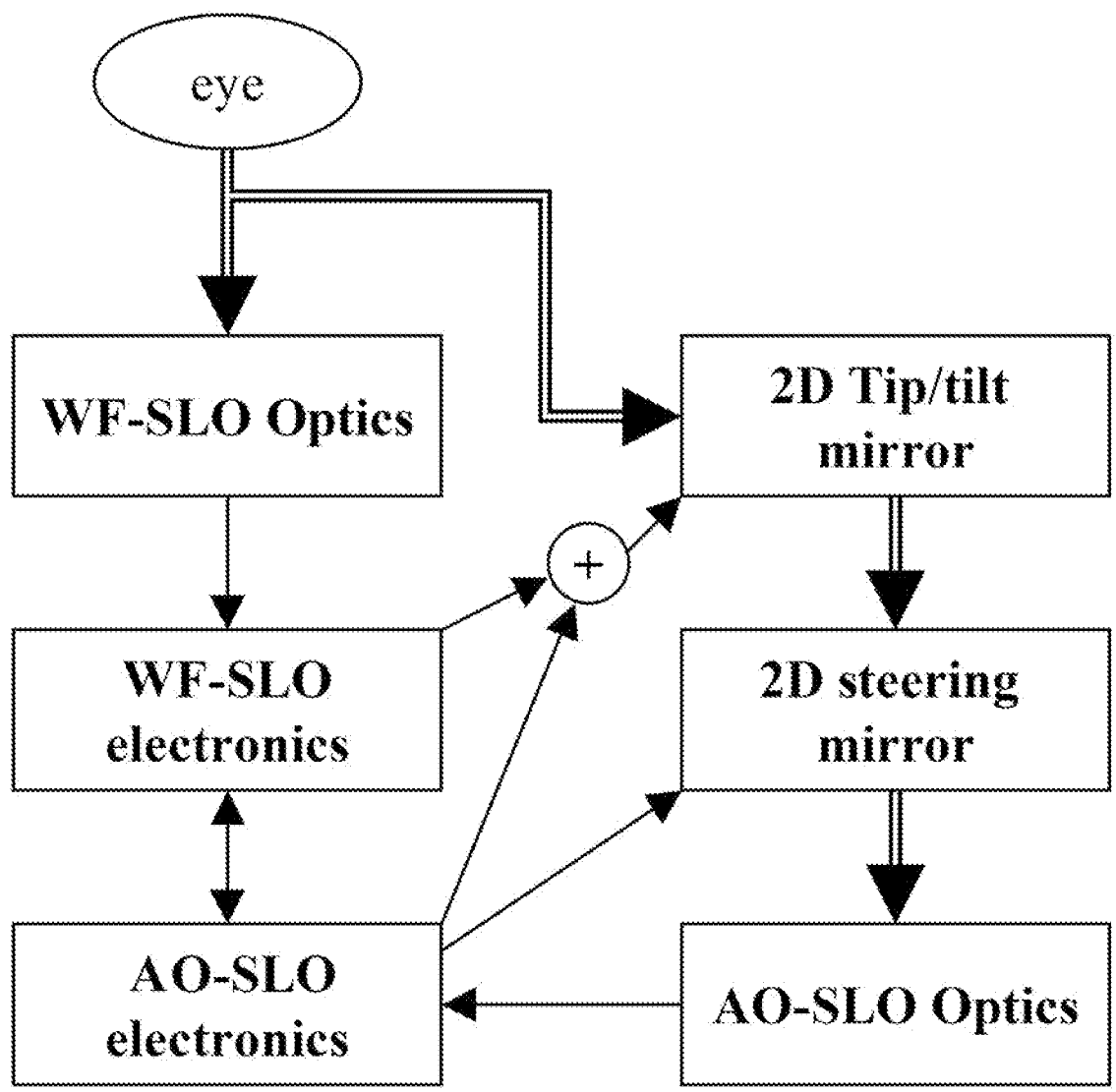
FIG. 2 shows one embodiment of a 2D tip-tilt mirror in open loop with WFSLO and in closed loop with AOSLO.
Figure 3:
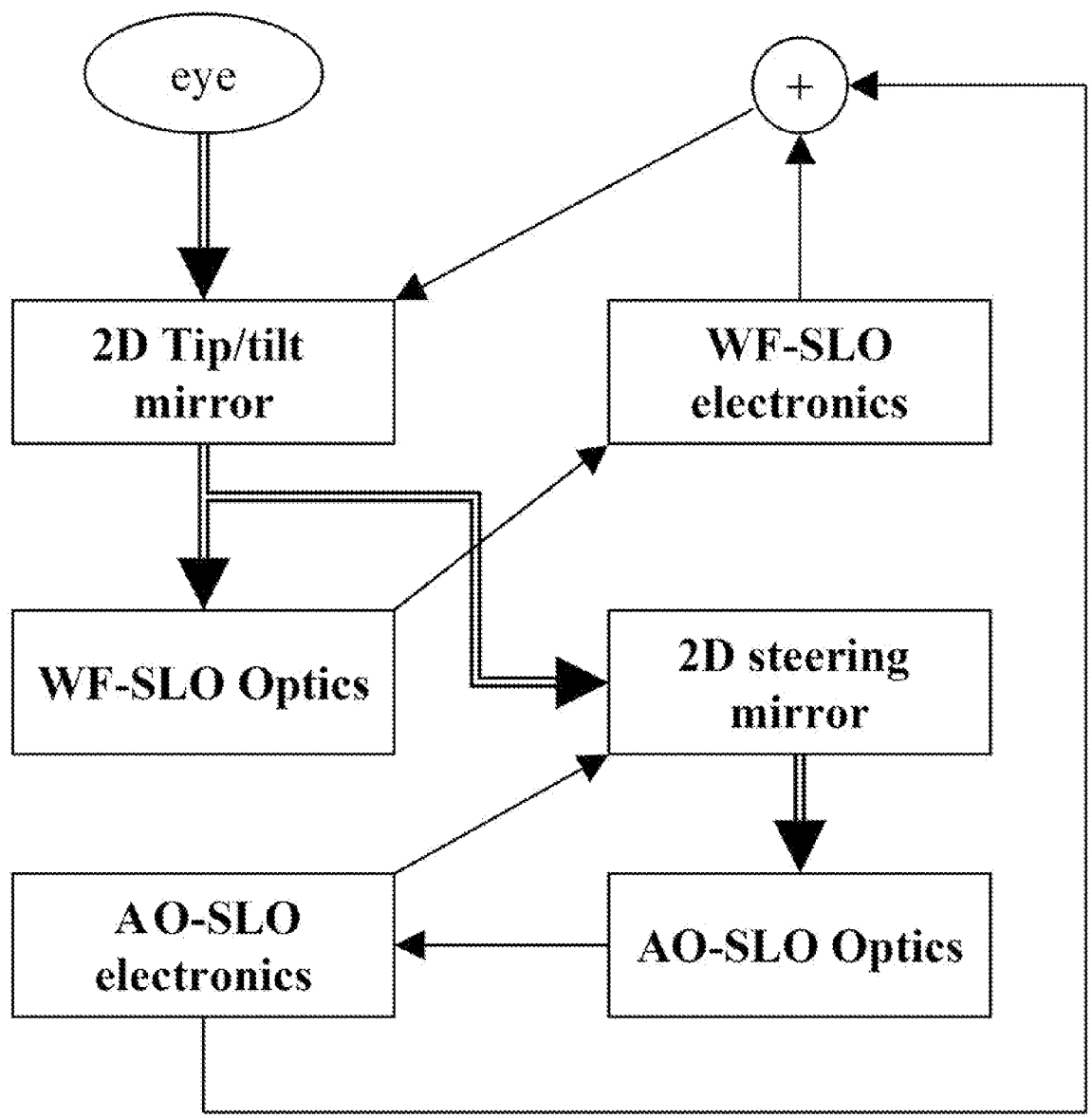
FIG. 3 shows another embodiment of a 2D tip-tilt mirror in closed loop with both WFSLO and AOSLO.

In FIG. 2 and FIG. 3, the double lines indicate a light path. The arrows on the double lines indicate that information is being determined by optical means from the eye. It is understood that both the wide field system (wide field scanning light ophthalmoscope (WFSLO)) and the small field high resolution imaging (scanning) system (AOSLO) use LASER light sources which transmit light to a point on the eye, as well as one or more photodetectors which receive LASER light reflected back from the eye. It is further understood that the WFSLO and AOSLO each include optical systems. The two separate optical systems (WFSLO and AOSLO) typically operate at different wavelengths. For example, in one exemplary embodiment, the WFSLO system employs a 890 nm LASER, while the AOSLO optical system uses a 790 nm LASER. The AOSLO optical system performs the high resolution imaging function, such as, scanning successive lines to form a high resolution image about a location on the eye. As further explained in more detail herein below, that location on the eye to be imaged is determined by the 2D steering minor, and held substantially in the same location on the eye during imaging by the tracking minor, also referred to herein as the 2D tip/tilt mirror. The single lines in the drawings generally indicate electronics connections. In the case of lines drawn between the AOSLO optics and the AOSLO electronics, and between the WFSLO optics and the WFSLO electronics, it is understood that despite the arrows of the block diagram, analog and/or digital information and control signals can flow in both directions as shown and explained with respect to FIG. 1. Also, it is understood that the single lines of FIG. 2 and FIG. 3 are simplified representations of, for example, the embodiment of FIG. 1, which shows more detail. For example, in FIG. 2 the single line from the AOSLO electronics to the 2D steering minor is a simplified representation of, for example, the AOSLO host PC control of the 2D steering minor via the AOSLO FPGA, AOSLO DAC, and analog control lines M and N to control the 2D operation of the 2D steering minor.

FIG. 2 shows one embodiment of a 2D tip-tilt minor which will work in open loop with WFSLO, and in closed loop with AOSLO. As described hereinabove, the AOSLO system creates one or more images (typically a plurality of images, such as over an x-y grid) used to later create an overall montage image of the eye. The LASER light of the AOSLO optics travels from the AOSLO optics through the 2D steering minor and the 2D Tip/tilt minor (the order of cascade of the minors in the optical path is unimportant) to the eye. Reflected light returns to the AOSLO optics via the same path in reverse direction. As explained hereinabove, and with respect to FIG. 1, the system commands the 2D steering minor to a location to be imaged (e.g. by control of the AOSLO PC via a DAC as shown in FIG. 1). Imaging data (typically one or more line scans) from both the WFSLO and the AOSLO systems are combined and processed to derive eye motion information as shown in more detail in FIG. 1. The summing symbol (circle with the plus symbol) of FIG. 2 symbolizes the process of combining the two motion inputs derived from the WFSLO and the AOSLO systems and the generation of a control signal to set the 2D Tip/tilt minor to preserve the intended location being scanned by the AOSLO system.

According to the contemplated embodiment of FIG. 2, the tracking WFSLO optics directly view the eye and the WFSLO optics LASER light does not follow the optical path defined by the 2D Tip/tilt minor and the 2D steering minor. The AOSLO system LASER light and reflected light follows the path defined by the 2D Tip/tilt minor and the 2D steering minor, where the 2D steering minor determines the location to be imaged, and the 2D Tip/tilt minor provides image stabilization responsive to a closed loop control which uses as feedback, information from both the WFSLO and the AOSLO systems.

FIG. 3 shows another contemplated embodiment of a 2D tip-tilt minor which works in closed loop with both WFSLO and AOSLO. The difference between FIG. 2 and FIG. 3 is that in FIG. 3 the LASER light of both the WFSLO and AOSLO systems travels through the optical path defined by the 2D Tip/tilt minor, and the WFSLO tracking system is thus also operated in closed loop mode. The advantage of operating the WFSLO system closed loop is somewhat improved eye motion tracking performance. Tradeoffs for the improved tracking accuracy include loop stability issues and/or a slightly increased risk of the WFSLO system closed loop losing its tracked position and momentarily going out of range temporarily opening the loop, or at an extreme, entirely losing the tracked location. It is contemplated that such risks can be minimized as the control processes continue to improve.

Techniques of the prior art used direct viewing of locations on the eye, followed by intensive post-processing of video or multiple images to improve image clarity. The end resolution of such techniques, which required very long patient imaging times, was generally worse than tens of µm. One hardware only approach did not succeed in reliable operation. Using the new system and method described herein (e.g. FIG. 1, and FIG. 2 or FIG. 3), initial digital images have been found to have a resolution of about 20 µm to 50 µm. Moreover through real-time or near real-time processing of multiple images in software, high resolutions of better than 1 µm have been achieved.

example: In one exemplar embodiment, light from the retina will be split into two channels, one channel to the wide FOV system, and the other channel to a tracking (tip/Tilt) minor, a steering minor, and then related to the small FOV system. To reduce latency and increase accuracy on controlling the tracking minor, the tracking minor is updated fast enough, e.g., in every millisecond to track eye motion. This exemplary embodiment uses a Xilinx FPGA board (ML506 or ML605, Xilinx, San Jose) to do data encoding and decoding. The selection of ML506 or ML 605 depends on functionality and cost. There is more flexible functionality and higher cost with ML605, and less flexible functionality and lower cost with ML506. Electronics of the wide FOV system is illustrated in FIG. 4.

Figure 4:
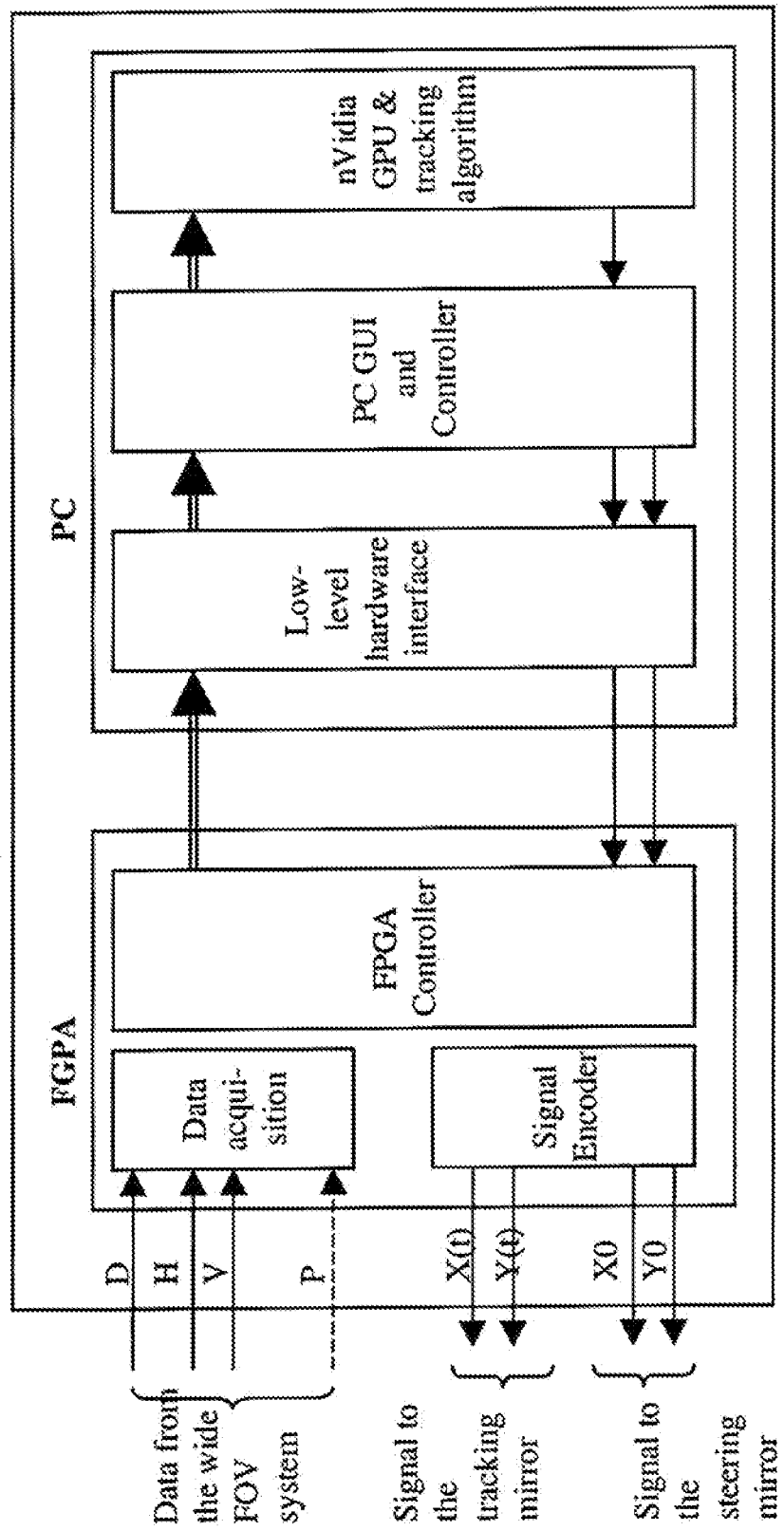
FIG. 4 shows a block diagram of an exemplary architecture of a wide FOV system.

FIG. 4 shows a block diagram of one exemplary architecture of a wide FOV system. In the architecture of FIG. 4, there are two modules: FPGA module and PC module. A) FPGA module will be responsible for real-time data acquisition from the optical system, flexible data buffering between FPGA and the host PC via a programmable PCI express (PCIe) controller, and data encoding to one or multiple D/A converters to control external devices such as the tip/Tilt tracking mirror and the steering mirror. Images from the wide FOV system can be either in 1) analog format with analog data, H-sync, and V-sync, or 2) digital format with digital data, H-sync, V-sync, and pixel clocks. In analog format, an A/D converter is used to digitize the images so that they can be sent to FPGA. In digital format, FPGA will be programmed to sample parallel or serial digital data from the wide FOV optical system. In either case, the digitized H-sync, V-sync and pixel clock will be used as common clocks throughout the whole FPGA application for buffering data from FPGA to PC through PCIe interface. These three clocks are also used to synchronize D/A converters which output eye motion signals to the tracking mirror and control the steering minor. The FPGA are programmed to control any resolution of off-shelf A/D (ADC) and D/A (DAC) converters, from 8 bits to 16 bits or even higher bits. B) PC module will be responsible for collecting images from FPGA, and send them to an nVidia GPU for data processing, and then upload eye motion signals and other control signals to FPGA. PC GUI and controller will manage the hardware interface between PC and FPGA, GPU image registration algorithm, and data flow between FPGA, PC CPU, and nVidia GPU. Architecture of the small FOV system can be very similar to that of the wide FOV system above, except that FPGA on the small FOV system will have more functionality such as ultra high accuracy laser beam modulation in 1-2 micrometer. However, in order to have more flexibility for future expansion of functionality, the same Xilinx FPGA board (ML506 or ML605) will be implemented. The functionality will include: 1) Real-time stabilized beam control to the retina. This feature allows future laser surgery with operation accuracy in several micrometers on the living retinas; and 2) Delivery of highly controllable image patterns to the retina for scientific applications; and 3) Real-time efficient montaging of retinal images.

Figure 5:
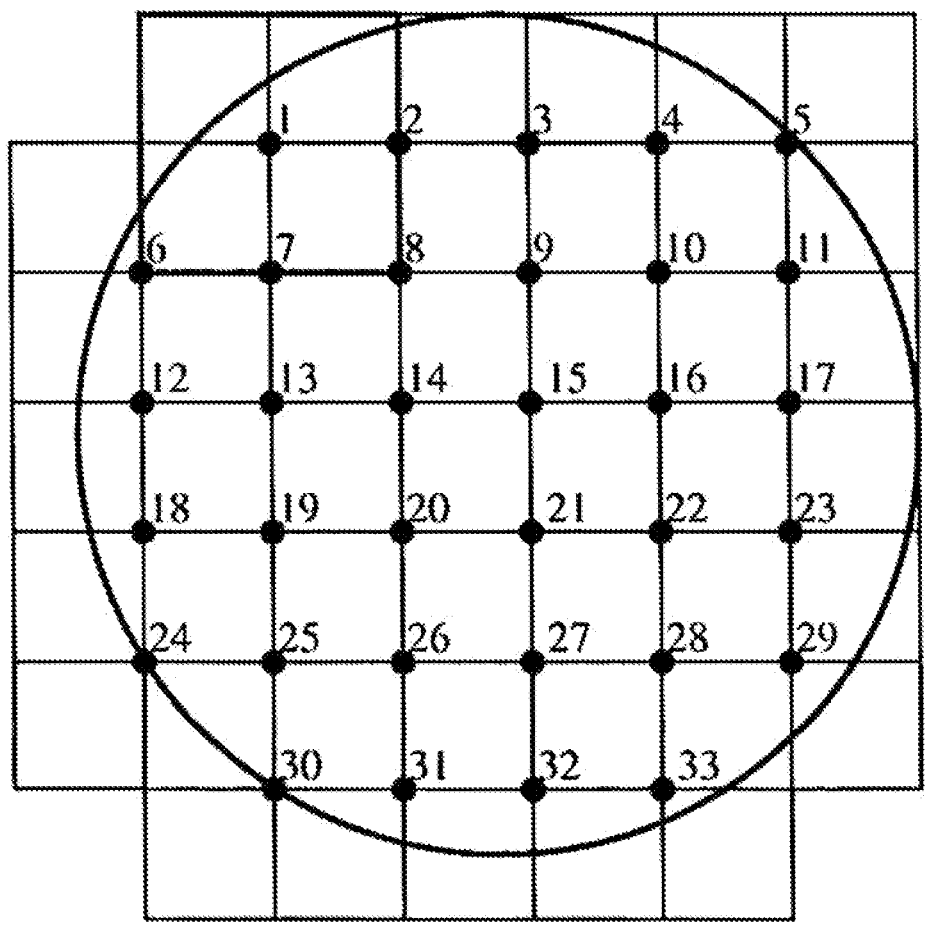
FIG. 5 shows a diagram illustrating one exemplary process for real-time montaging.

FIG. 5 shows a diagram illustrating one exemplary process of real-time montaging. The circled area is the retina covered by the wide FOV system with low spatial resolution, and the rectangular area is covered by the small FOV system with high spatial resolution. To achieve a high-resolution image montage from the retina, the two systems will be programmed to move the steering mirror to the locations of the exemplary black dot position labeled 1, 2, . . . , 33, one at a time. In each location, the tracking minor will remove large eye motion, and the registration algorithm on the small FOV system removes the residual eye motions in real time and then registers the images in real time. The software and hardware uses only 10-15 seconds to register images in each location. The steering minor will be automatically armed to the next location after the current one is finished. When the steering mirror sweeps through all 33 (or a different number) locations, the software will automatically generate a big montage of the retina image. The adjacent locations should have overlap. The amount of overlapping depends on the residual eye motion on the small FOV system.

Figure 6:
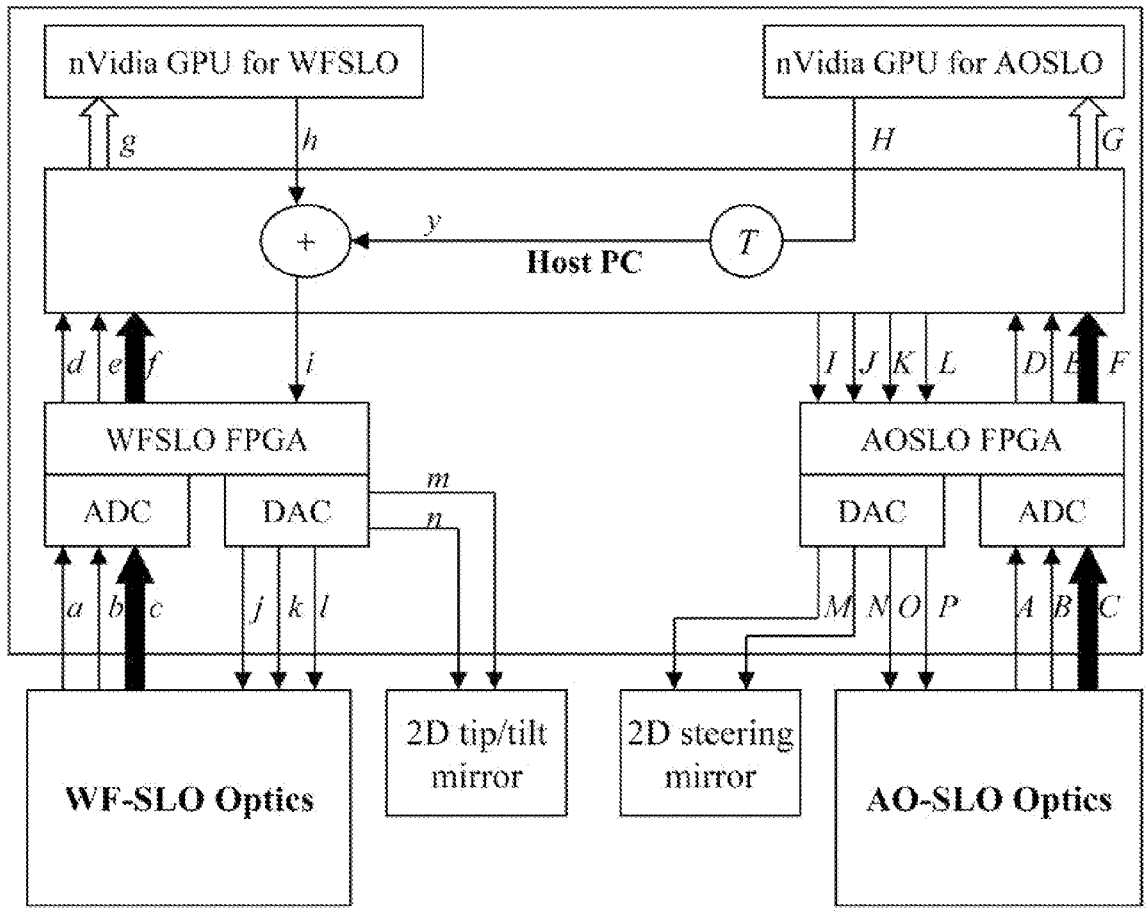
FIG. 6 shows a block diagram of a real-time ophthalmoscope system for imaging an eye with independent scanner signals.

FIG. 6 shows a block diagram of a real-time ophthalmoscope system for imaging an eye with independent scanner signals.

Figure 7:
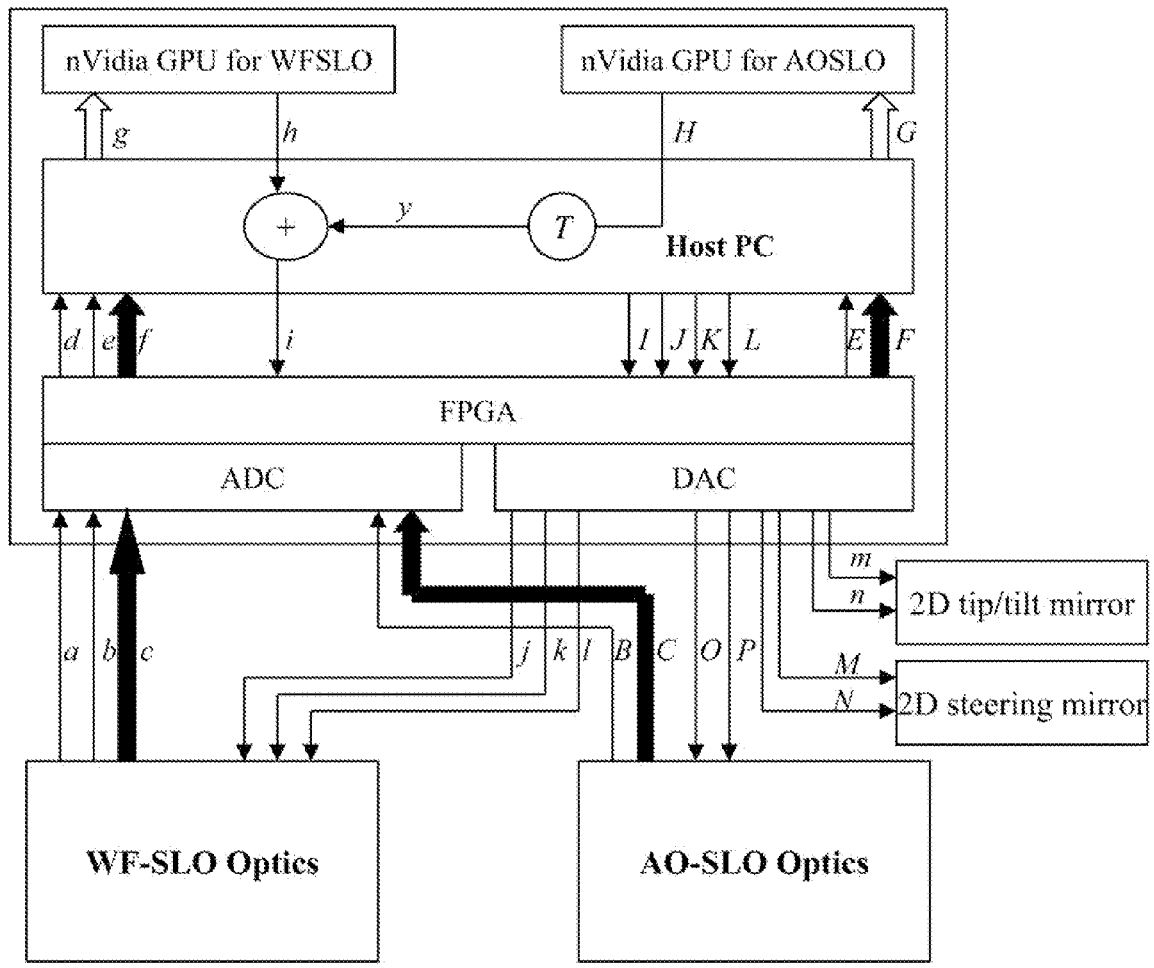
FIG. 7 shows a block diagram of a real-time ophthalmoscope system for imaging an eye with synchronized scanner signals.

FIG. 7 shows a block diagram of a real-time ophthalmoscope system for imaging an eye with synchronized scanner signals.

One exemplary mirror suitable for use as the 2D tip/tilt mirror is the model S-334.2SL available from Physik Instrumente of Karlsruhe, Germany. The S-334.2SL is a high-precision high-speed two-axis mirror where each axis has a piezoelectric actuator. Suitable DACs for controlling mirrors include the DAC2904 and DAC5672 available from Texas Instruments of Dallas, Texas. One exemplary FPGA is the Xilinx ML506 FPGA available from Xilinx of San Jose, California. One exemplary minor suitable for use as the steering minor is the model 6M2003X-S available from Cambridge Technology Inc. of Bedford, Mass.

Contemplated applications of the system and method described herein include Adaptive Optics Scanning Laser Ophthalmoscope (AOSLO), Scanning Laser Ophthalmoscope (SLO), and most scanning-based imaging systems.

Any suitable type of computer (e.g. any suitable type of desktop computer, computer workstation, or more likely any suitable type of embedded computer, microcomputer or embedded processor) can be used for the wide field SLO computer and the wide field SLO computer. Any suitable logic element in software, firmware, or hardware can be used in place of the exemplary field programmable gate array (FPGA) elements. In some embedded computer embodiments, ADCs and/or DACs can be supplied as built in components into a microcomputer. It is also unimportant to the system if the either the small field SLO or wide field SLO included the ADC and/or DAC functions within the SLO assembly and communicated by digital means with either of the SLO computers.

Components such as the wide field SLO and/or the small field SLO and/or components such as the Tip/tilt minor and/or the steering minor can be communicatively coupled to each other and/or one or more computers by any suitable means. For example, there can be analog and/or digital signals coupled by any suitable wired, fiber optic, and/or wireless means. In some embodiments, one or more components might similarly use any suitable standard serial or parallel digital connection, such as, for example, RS-232, RS-422, GPIB, etc. It is also understand that cards and/or circuit boards can be connected via any suitable crate or bus structure either inside a computer, inside a dedicated or shared crate, or in any other suitable packaging and connectivity scheme. All of the above means for communicatively coupling components to one another and/or to a computer (including optical fibers) are defined herein as falling within our definition of the term "electrically coupled".

While the exemplary embodiments show a separate small field SLO computer and wide field SLO computer, it is contemplated that in other embodiments, the system can be built around one common computer. It is unimportant that there be two separate computers.

Any software (e.g. process algorithms) described herein are typically provided on a computer readable non-transitory storage medium as non-transitory data storage which includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

All references cited herein are incorporated herein by reference in their entirety and for all purposes to the same extent as if each individual publication, patent or patent application was specifically and individually indicated to be incorporated by reference in its entirety for all purposes.

What is claimed is:

1. A real-time ophthalmoscope system for imaging an eye comprising:
   a wide field scanning light ophthalmoscope (SLO) electrically coupled to a computer, said wide field SLO configured for wide field imaging of said eye;
   a small field SLO electrically coupled to said computer, said small field SLO configured for high resolution imaging of said eye;
   a 2D tracking mirror electrically coupled to said computer and disposed in an optical path between said small field SLO and said eye;
   a 2D steering mirror electrically coupled to said computer and also disposed in said optical path between said small field SLO and said eye; and
   wherein said system is configured to acquire a plurality of small field images at a plurality of locations on said eye as defined by said 2D steering mirror, each of said small field images stabilized for a motion of said eye by said 2D tracking mirror.

2. The system of claim 1, further comprising a closed loop control of said tracking mirror by said small field SLO.

3. The system of claim 1, wherein said 2D tracking mirror is further disposed in an optical path between said wide field SLO and said eye, and further comprising a closed loop control of said tracking mirror by said wide field SLO.

4. The system of claim 1, wherein said 2D tracking mirror comprises a Tip/tilt mirror.

5. The system of claim 1, wherein a position of said tracking mirror is updated at a rate of about 1 kHz.

6. The system of claim 1 wherein at least one of said small field SLO computer and said wide field SLO computer further comprises a graphics processing unit (GPU).

7. The system of claim 1, wherein said wide field SLO is synchronized with said small field SLO.

8. The system of claim 1, wherein said small field SLO comprises an adaptive optics scanning light ophthalmoscope (AOSLO).

9. The system of claim 1, wherein said wide field SLO comprises wide field scanning light ophthalmoscope (WF-SLO).

10. The system of claim 1, wherein said computer comprises a wide field SLO computer and a small field SLO computer, and said a wide field SLO is electrically coupled to a wide field SLO computer, said small field SLO is electrically coupled to said small field SLO computer which is communicatively coupled to said wide field SLO computer, and said 2D tracking minor is electrically coupled to said wide field SLO computer and said 2D steering minor is electrically coupled to said small field SLO computer.

11. The system of claim 1, wherein said wide field SLO is synchronized with said small field SLO.

12. A method for imaging an eye comprising the steps of:
a) providing a wide field scanning light ophthalmoscope (SLO) electrically coupled to a wide field SLO computer, said wide field SLO configured for wide field imaging of said eye, a small field SLO electrically coupled to a small field SLO computer communicatively coupled to said wide field SLO computer, said small field SLO configured for high resolution imaging of said eye, a 2D tracking minor electrically coupled to said wide field SLO computer and disposed in an optical path between said small field SLO and said eye, and a 2D steering minor electrically coupled to said small field SLO computer and also disposed in said optical path between said small field SLO and said eye;
b) pointing said small field SLO at a location on said eye to be imaged;
c) stabilizing said small field SLO against a movement of said eye by use of said 2D tracking mirror controlled by at least said wide field SLO;
d) imaging said location by said small field SLO to provide a stabilized image of said location;
e) repeating steps b to d until a desired number of said stabilized images of a plurality of locations are obtained; and
f) montaging a plurality of said images to form a stabilized image of said eye.

13. The method of claim 12, further comprising after step d, the step of stabilizing further said stabilized image by a digital stabilization method.

14. The method of claim 13, wherein said digital stabilization method is performed in software.

15. The method of claim 12, wherein said step c further comprises stabilizing said small field SLO against a movement of said eye by use of said 2D tracking minor controlled by both said small field SLO and said wide field SLO.

* * * * *